(12) United States Patent
Glott et al.

(10) Patent No.: US 11,298,038 B2
(45) Date of Patent: Apr. 12, 2022

(54) IN-VIVO PRESSURE MONITORING SYSTEM (71) Applicant: SINTEF TTO AS, Trondheim (NO)

(72) Inventors: Thomas Glott, Snaroya (NO); Ingelin Clausen, Oslo (NO)

(73) Assignee: SINTEF TTO AS., Trondheim (NO)

( * ) Notice: Subject to any disclaimer, the term of this patent is extended or adjusted under 35 U.S.C. 154(b) by 132 days.

(21) Appl. No.: 15/030,105

(22) PCT Filed: Oct. 23, 2014

(86) PCT No.: PCT/EP2014/072704
§ 371 (c)(1),
(2) Date: Apr. 18, 2016

(87) PCT Pub. No.: WO2015/059217
PCT Pub. Date: Apr. 30, 2015

(65) Prior Publication Data
US 2016/0262642 A1 Sep. 15, 2016

(30) Foreign Application Priority Data
Oct. 25, 2013 (EP) .................................... 13190369

(51) Int. Cl.
*A61B 5/03* (2006.01)
*A61B 5/00* (2006.01)
(Continued)

(52) U.S. Cl.
CPC ............ *A61B 5/035* (2013.01); *A61B 5/0002* (2013.01); *A61B 5/0215* (2013.01); *A61B 5/031* (2013.01);
(Continued)

(58) Field of Classification Search
CPC ..... A61B 5/035; A61B 5/7203; A61B 5/7246; A61B 5/746; A61B 5/0215; A61B 5/0002; A61B 5/6852; A61B 5/205; A61B 5/036; A61B 5/03; A61B 5/031; A61B 5/033; A61B 5/4836; A61B 2560/0247; A61B 2560/0252; A61B 2562/0247; A61N 1/36007
See application file for complete search history.

(56) References Cited

U.S. PATENT DOCUMENTS 5,167,237 A * 12/1992 Rabin .................... A61B 5/205
128/836
5,191,898 A 3/1993 Millar
(Continued)

FOREIGN PATENT DOCUMENTS

GB 2308888 A 7/1997

OTHER PUBLICATIONS

The above references were cited in an International Search Report, which is enclosed, that issued in the corresponding International Patent Application No. PCT/EP2014/072704.

*Primary Examiner* — Devin B Henson
(74) *Attorney, Agent, or Firm* — Cowan, Liebowitz & Latman, P.C.; Mark Montague (57) ABSTRACT

A system for in-vivo monitoring of pressure of a body fluid. The system comprises a delivery component and an elongate
(Continued)

sensor delivery member shaped so as to pass through the delivery component when it has been inserted in to a patient. A first pressure sensor is positioned at a distal end of the delivery member.

24 Claims, 4 Drawing Sheets

(51) Int. Cl.
 *A61B 5/20* (2006.01)
 *A61N 1/36* (2006.01)
 *A61B 5/0215* (2006.01)

(52) U.S. Cl.
 CPC .............. *A61B 5/036* (2013.01); *A61B 5/205* (2013.01); *A61B 5/4836* (2013.01); *A61B 5/6852* (2013.01); *A61B 5/7203* (2013.01); *A61B 5/7246* (2013.01); *A61B 5/7282* (2013.01); *A61B 5/746* (2013.01); *A61N 1/36007* (2013.01); *A61B 2560/0252* (2013.01); *A61B 2562/0271* (2013.01)

(56) References Cited

U.S. PATENT DOCUMENTS

| | | | | |
|---|---|---|---|---|
| 5,683,422 A | * | 11/1997 | Rise | A61N 1/36171 |
| | | | | 607/2 |
| 6,248,080 B1 | * | 6/2001 | Miesel | A61B 5/0215 |
| | | | | 600/311 |
| 6,296,615 B1 | * | 10/2001 | Brockway | A61B 5/036 |
| | | | | 600/486 |
| 7,195,594 B2 | * | 3/2007 | Eigler | A61B 5/0215 |
| | | | | 600/300 |
| 9,795,336 B2 | * | 10/2017 | Chung | A61B 5/6823 |
| 2002/0151816 A1 | * | 10/2002 | Rich | A61B 5/0031 |
| | | | | 600/547 |
| 2006/0247725 A1 | * | 11/2006 | Gerber | A61N 1/36007 |
| | | | | 607/41 |
| 2008/0103408 A1 | * | 5/2008 | Denton | A61B 5/01 |
| | | | | 600/549 |
| 2010/0057046 A1 | * | 3/2010 | Stevens (Nee Webber) | |
| | | | | A61B 5/02055 |
| | | | | 604/507 |
| 2010/0152608 A1 | * | 6/2010 | Hatlestad | A61B 5/0028 |
| | | | | 600/561 |
| 2010/0222637 A1 | | 9/2010 | Kassab | |

* cited by examiner

IN-VIVO PRESSURE MONITORING SYSTEM

The present invention relates to an in-vivo pressure monitoring system.

There are many locations within a human or animal body where there are medical benefits in being able to monitor the ambient pressure in fluid or tissue. For example, it can be extremely beneficial in understanding the wellbeing of a patient and understanding the effectiveness of any treatment to the pressure in a patient's cranial fluid, within their bladder, muscle compartments, or within their circulatory system.

Because of the benefits of such monitoring pressure monitoring systems have been developed which can be inserted in to the body of a user to provide pressure readings.

One example is a system in which a fluid filled catheter is inserted via the urinary tract in to the bladder. The fluid in the catheter will transmit pressure to an external transducer located outside the patient. The bladder is then filled with saline with simultaneous pressure recording. A balloon attached to a fluid filled catheter is inserted into the rectum for recording of reference pressure.

Such systems have provided significant benefits in terms of improved pressure readings which a medical practitioner can then use to assess the condition of the patient. However, they also have significant disadvantages.

For example, a system of the type described above is extremely uncomfortable for a patient in that it requires insertion of a relatively large catheter, and restricts the movement of the user quite significantly whilst this Is in place. Furthermore, such systems do not necessarily provide true indication of bladder pressure, because it can only be in place for a limited period of time during which the bladder will not have been through a complete cycle of having been filled and emptied. In addition, such a system is sensitive to movement by the patient, such movement potentially generating pressure variations that the system is unable to compensate for.

Accordingly, there is a need for provision of a system which can be employed with the patient to improve the monitoring of the pressure of a bodily fluid with reduced discomfort to the patient. Furthermore, there is a need to provide a system which can provide long term monitoring so that pressure readings over an extended period of time can be provided to ensure a true representation of the fluid pressures and therefore give a better representation of the condition of a patient and the effectiveness of any treatment. In addition, there is a need to provide a system which can compensate for factors which may affect any pressure reading which are not actually directly linked to a patient's condition, such as digestion, change in body position, or movement by the patient or external pressure or temperature changes. There is also a need to provide a system which can assist in longer term monitoring of pressure and assist in treatment of a patient's condition. The present invention seeks to meet at least some of these needs.

According to the present invention there is provided a system for in-vivo monitoring of ambient pressure in a body fluid or tissue, the system comprising:
  a delivery component;
  an elongate sensor delivery member shaped so as to pass through the delivery component when it has been inserted in to a patient; and
  a first pressure sensor positioned at a distal end of the delivery member.

The delivery component may be a catheter. The system may further comprise a second pressure sensor configured to be inserted subcutaneously in to a patient in use. In such a configuration the system may further comprise means for receiving data for the second sensor and for comparing it to pressure data for the first sensor. Such a comparison provides a final signal that has been adjusted to compensate for external pressure on the fluid or tissue for which pressure is being monitored, that external pressure having been generated by patient movement or atmospheric pressure variation, for example, as such effect will have been read by both sensors.

The system may further comprise a temperature sensor such that pressure data from the first sensor can be adjusted to remove any temperature related effects.

The delivery member may have communication means and power supply means formed therein such that the sensor can be provided with power and the output of the sensor can be passed through the elongate member to external processing means. The output of the sensor(s) element can be passed through the elongate member to a subcutaneous processing means. Alternatively, the first and the second sensor element may have wireless communication means for communication with a subcutaneous processing means. The subcutaneous processing means then may have wireless communication means for communication with an external data receiving/handling device.

The system of the present invention may be connected to an alarm device to provide warning if a pressure detected by the system exceeds a predetermined amount. In addition to this, or as an alternative thereto, this can be a system configured to activate a nerve stimulation device connected to the patient to which the system is itself connected to stimulate the nervous system of a user to act in response to a pressure variation detected by the system.

With the system of the present invention, by use of a simple cannula and delivery member in combination, it is possible to insert a pressure sensor in to a patient very simply and with far less discomfort than with prior art systems. Furthermore, it is possible to provide a system which can be retained within the patient for far longer periods of time, for example days rather than hours, without reducing patient mobility. This provides the additional benefits that pressure data can be obtained over far longer periods of time providing far more reliable and consistent data for assessment for patient's condition. The system of the present invention, when provided with additional sensors also provides more accurate data that compensates for potential errors generated by variations in temperature, atmospheric pressure, or patient movement, for example.

One example of the present invention will now be described with reference to the accompanying drawings, in which.

Figure 1:
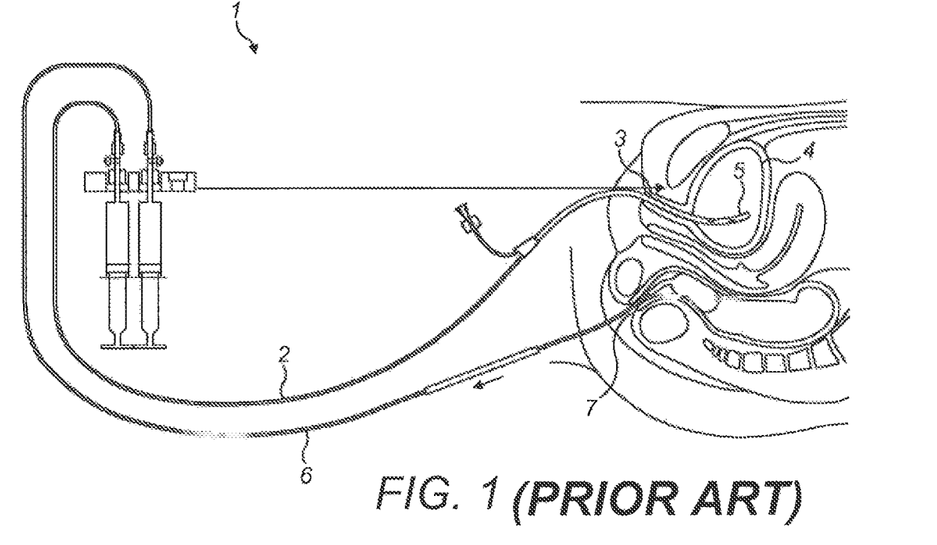
FIG. 1 is a schematic diagram of an example prior art in-vivo pressure monitoring system.

Referring to FIG. 1, a system 1 according to the prior art comprises a catheter 2 which is passed, in use, through the urinary tract 3 and in to the bladder 4 of a patient. Positioned at the distal end of the catheter 2 is a pressure sensor 5. A second balloon catheter 6 is provided and is passed, in use, in to the rectum 7 of the patient. In use fluid may be provided via the catheter 2 in to the bladder 4 to fill the bladder and/or the balloon catheter 6 inflated to apply pressure to the bladder 4 to retain the catheter in place. Readings are taken from the pressure sensor 5 during the generation of pressure within the bladder 4 to provide an indication of pressure levels within the bladder so that an assessment of a patient's condition can be provided.

As mentioned above, such a system has significant disadvantages. First of all, insertion of the catheter through the urinary tract 3 can cause discomfort to a patient. Furthermore, artificial generation of pressures on the bladder 4 do not necessarily provide accurate results, but in the system 1 of the type shown such artificial creation of pressures, be it through application of fluid directly to the bladder 4 or by application of pressure via the balloon catheter 6 in the rectum 7, to retain the catheter's position, is required. This is because the invasive nature of the equipment and the discomfort generated to a patient are such that the system can only be used on a patient for a maximum of a few tens of minutes. Furthermore, in such systems there is little compensation for effects that are not directly related to the bladder 4 but which may affect the output of the sensor 5. For example, digestion, change in body position and movement of the patient can all affect pressure within the bladder 4, as can variations in atmospheric pressure and temperature.

Figure 2:
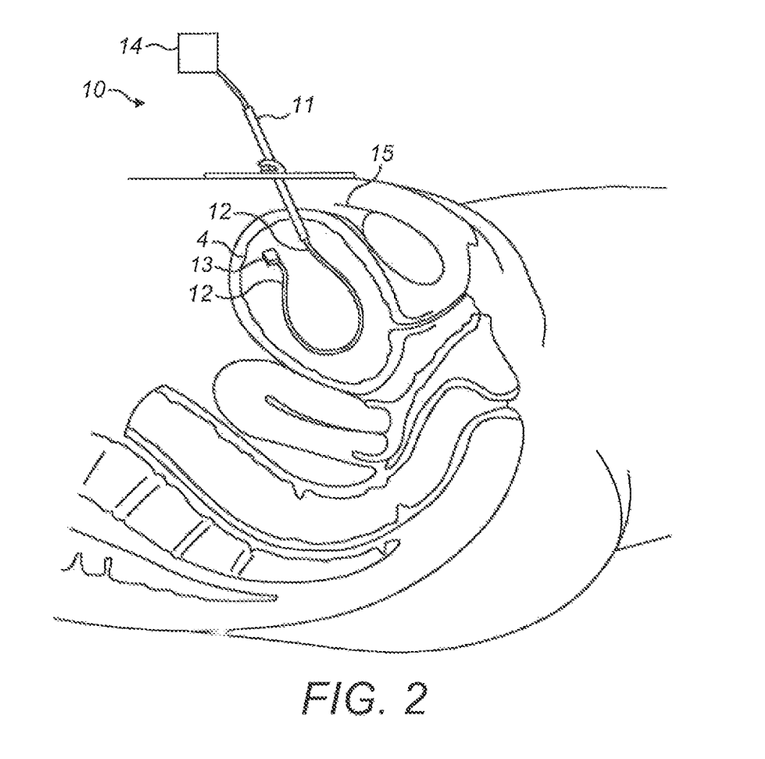
FIG. 2 is a schematic diagram showing an example system according to the present invention.
Figure 3:
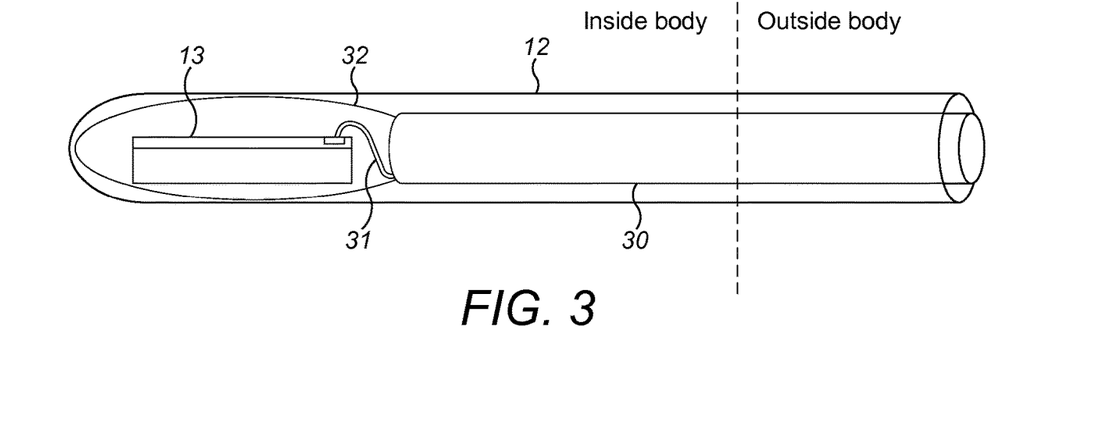
FIG. 3 is a schematic cross-sectional view of a sensor and delivery device employed in the invention.
Figure 4:
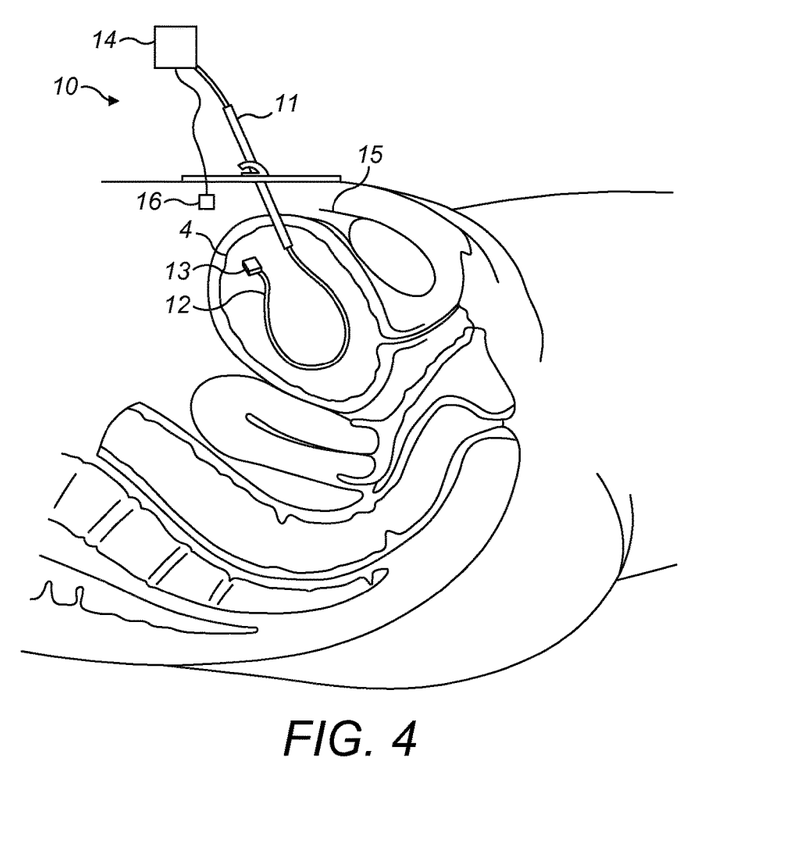
FIG. 4 is a schematic diagram showing a further example system according to the present invention.

FIG. 2 is a schematic diagram of a system 10 in accordance with the present invention. The system 10 of the present invention comprises a delivery component, in this example a cannula 11 and delivery catheter 12. Positioned at a distal end of a delivery catheter 12 is a pressure sensor 13. The sensor 13 and delivery device 12 is a micro electro mechanical system (MEMS) integrated in a hollow flexible tube made out of biocompatible material. The sensor 13 and delivery device have a diameter of less than 1.0 mm, it is possible to insert the device using a simple minimally invasive technique. FIGS. 3 and 4 show these components in more detail, they are formed from a flexible, hollow tube containing the pressure sensor element 13 connected electrically and mechanically to a flexible printed circuit board. The major part of the components, including the sensor 13, is placed inside the subject, while the distal end is connected to an electronic front end (FE) module placed externally on the body including a signal processing component 14 (shown in FIG. 4).

In use the system 10 of the present invention is operated as follows. Firstly, the cannula 11 is inserted through the abdominal wall 15 and in to the bladder 4. The delivery catheter 12 is then inserted in to the cannula and in to the bladder 4 so that the sensor 13 is positioned within the bladder 4. The signal processing component 14 is attached to the patient also so the patient is then mobile and can move about as normal. Pressure readings can then be taken from the sensor 13 and processed by the signal processing component 14 over a significant period of time, hours or possibly even days. Accordingly, pressure data can be obtained by the signal processing component 14 over a complete emptying and filling cycle of the bladder to provide far more data to a physician than is available with any prior art system. The cannula 11 of the system 10 of the present invention is a relatively standard cannula. The sensor 13 can be one of a number of sensors, but is, for example, a sensor of the type disclosed in "I. Clausen, et al., "A miniaturized pressure sensor with inherent biofouling protection designed for in vivo applications," in 33rd Annual International Conference of the IEEE Engineering in Medicine and Biology Society, Boston, Mass. USA, 2011, pp. 1880-1883.". The delivery catheter 12, as it does not have to deliver any fluids in to the bladder, can be of a relatively narrow diameter, which simplifies insertion and reduces the size requirements of the cannula.

As will be appreciated, the example shown in FIG. 2 is inserted in to a bladder 4. However, a similar approach could be used to insert the sensor 13 in to another body cavity or tissue for pressure sensing another part of a patient's body. It could, for example, be inserted in to the cranial fluids to measure cranial fluid pressure using a similar delivery component 11 and delivery catheter 12. The use of cannula is not relevant in this example. Instead, the sensor 13 is integrated in the tip of the catheter, which is inserted to drain away excessive brain fluid to e.g. the abdomen.

The signal processing component 14 may further comprise an additional pressure sensor and/or temperature sensor 16 so that data can be collected to compensate for variations in atmospheric pressure and temperature to improve the accuracy of the data from the pressure sensor 13.

FIG. 4 shows a further example system 10 according to the present invention. This example has many components in common with the example of FIG. 2, and where this is the case, components have been numbered identically. Here however, a second pressure sensor 16 is provided with the system 10, that pressure sensor 16 being arranged to be inserted subcutaneously in to the patient. It also connected to the processing component 14. In this example, the second pressure sensor 16 provides data on the pressure adjacent to the bladder 4 in the abdominal wall. This pressure data is fed to the signal processing component 14 for assessment in combination with the data received from the first pressure sensor 13.

Figure 5:
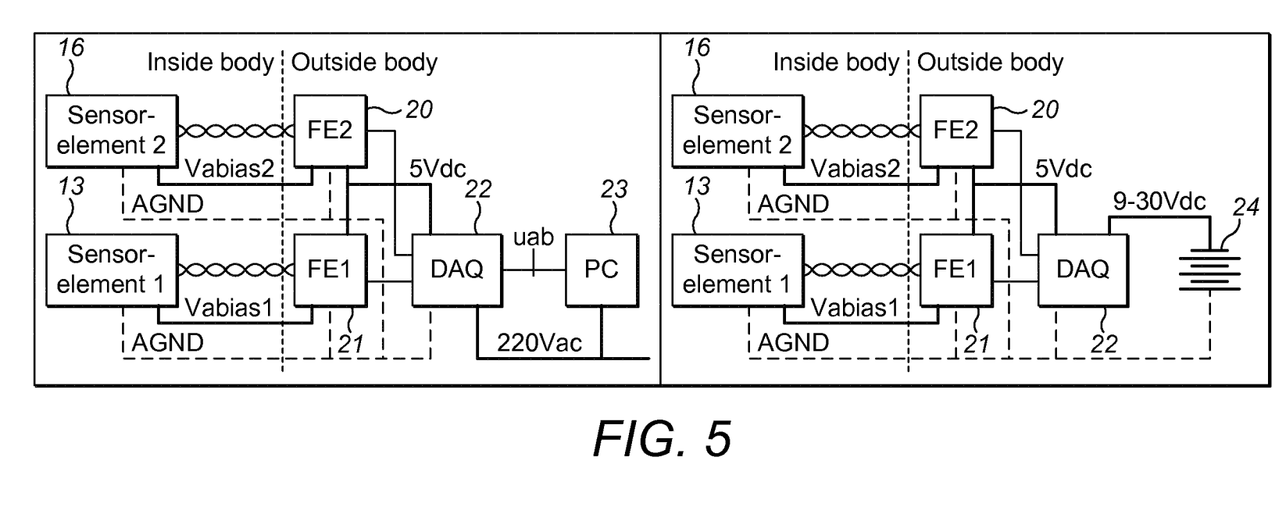
FIG. 5 is a schematic diagram showing example signal processing circuitry for use in the invention.

Data from the second pressure sensor 16 can be used to compensate for pressure generated by user movement and/or the atmosphere that might affect the bladder 4 but which is not directly related to pressure of fluid within the bladder. This enables the signal processing component 14 to compensate for such movements by providing data for analysis by a physician. It can also be used to compensate for atmospheric condition variations, for example. The signal of interest is the differential signal between the first 13 and the second sensor 16. As the atmospheric condition and also change in body position affect both signals in the same way, so in most cases no other compensation is required. FIG. 5 shows example system configurations with two sensors. The target signal from sensor 13 and the reference signal from the second sensor 16 are transmitted to two separate electronic modules 20.21 and from there further transmitted to an external data module (DAQ) 22. Measurement data are either transferred from the DAQ module 22 via USB to a PC 23 or stored on a SD-memory card 24.

With all of the systems of the present invention it is possible for the signal processing component 14 to be configured to issue an alarm if excessive pressure is detected either pressure sensor 13, or if a pressure threshold is exceeded for a predetermined period of time. Such an alarm can be used to advise a physician of a serious medical condition, or can be used by a patient to remind them to empty their bladder, for example. In addition to the provision of such an alarm, or as an alternative thereto, the signal processing component 14 may be configured to trigger a nerve stimulation component under certain pressure conditions, that nerve stimulation component then stimulating a patient's nervous system to encourage it to empty the patient's bladder, for example.

Figure 6:
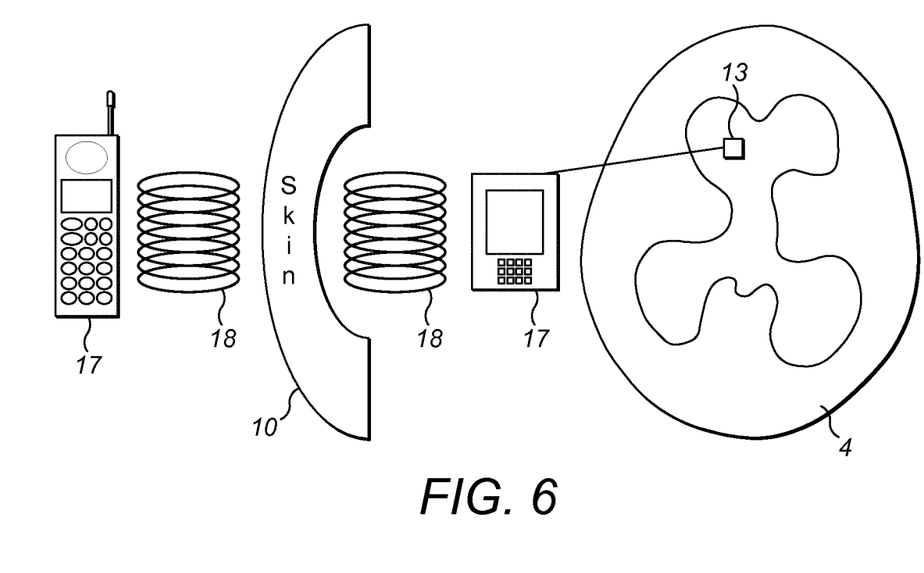
FIG. 6 is a schematic diagram of a yet further example of the invention in which wireless communication with the sensor is provided.

FIG. 6 shows an alternative system 10 of the present invention further comprising wireless communication means 17 for receiving data from the first 13 and/or second 16 pressure sensors. The received data is then transmitted, either by wired or wireless means to the signal processing component 14. With such a system it is possible for the sensor 13 to be left in the bladder 4 or other body cavity and the delivery catheter 12 removed, together with removal of the cannula 11. This yet further reduces patient discomfort whilst allowing the pressure sensor to remain within the body cavity to provide long term pressure readings. With such a configuration the first sensor 13 and/or the second sensor (not shown), may have their own power supply and/or maybe configured to be charged capacitively or inductively by the wireless communication component. With such configuration a number of different wireless communication techniques are possible such as inductive methods, or other methods where the signal transmitter is "short-circuiting"/changing an EM-field set up by an external power source (and data receiver).

The system of the invention is to be comprehensive in all aspects, diagnostic, monitoring and therapeutic, and can be used throughout a process treatment of a patient. In general, the first stage in the process is to explore whether there is a pressure related problem or not. If there is a suspected pressure related problem, long-term monitoring may be needed to clarify the extent and severity of the problem under physiological conditions in the second stage. The third stage will involve therapeutic intervention with feedback systems to a device releasing medication, alarm system or electrical stimulation.

The process would have a schematic progression for all stages A first stage is diagnostic evaluation with sensors placed in fluid and/or tissue connected to external recording devices. Typical recording time will be less than 60 minutes.

A second stage is monitoring during physiological conditions with sensors placed in fluid and/or tissue connected to small external recording devices adapted for ambulatory use. Typical recording time will be 24-48 hours. A next stage is therapeutic intervention with sensors placed in fluid and/or tissue and implantable recording device connected to device. Expected duration of this stage will be from weeks up to several years.

As mentioned above, the system of the present invention provides significant benefits over the prior art systems in terms of ease of insertion in to a patient, as well as the ability to provide long term measurements, and allow independent movement for a patient with which the system is used. Furthermore, it also enables for provision of a system in which a patient can be assisted in control of their own bladder movement or control of their medical condition that can be monitored based on the fluid for which pressure is being detected. Furthermore, it also enables the possibility of a system in which auto stimulation of a body function or auto triggering of a medical device can be provided in a simple and effective manner based upon the monitored pressure.

The invention claimed is:

1. A system for in-vivo monitoring of pressure of a body fluid in an interior volume of a urinary bladder of a patient, the system comprising:
   a delivery component of a cannula type being configured to penetrate through an abdominal wall of the patient and further through a location on the bladder wall into the interior volume;
   a flexible elongate sensor delivery member shaped so as to pass through the delivery component when the delivery component has penetrated the bladder wall in order to allow the sensor delivery member to enter into the interior volume of the bladder; and
   a first pressure sensor being positioned at a distal rounded end region of the delivery member that is inserted into the bladder interior of the patient, the first pressure sensor measuring and providing a first pressure data of the body fluid in the bladder;
   a second pressure sensor configured to be inserted subcutaneously into the abdominal region of the patient, the second pressure sensor measuring and providing a second pressure data that may influence the first pressure data; and
   an external signal processing component located remotely from the abdominal wall surface of the patient, configured to receive and process the first pressure data and the second pressure data while the patient is engaged in ambulatory movement, calculate a differential signal between the first pressure data and the second pressure data and automatically adjust the first pressure data based on the calculated differential while the patient is engaged in ambulatory movement, thereby compensating for variations in pressure caused at least in part by the patient's ambulatory movement, and
   the adjustment of the first pressure data based on the calculated differential with the second pressure data being performed based on the readings from the first and second pressure sensors, as received and adjusted while the patient is engaged in the ambulatory movement, and the adjustment automatically compensating for the internal organ activity caused by the ambulatory movement of the patient.

2. The system of claim 1, wherein the external signal processing component provides an output to a user based upon the received first pressure data and the calculated differential signal.

3. The system of claim 1, wherein the first pressure data and the second pressure data are received by the external signal processing component through separate electronic modules.

4. The system of claim 1, wherein the sensor delivery member and the first pressure sensor have lesser diameter than the delivery component, and wherein the first pressure sensor is integrally connected to a distal tip part of the sensor delivery member during insertion through the delivery component into the patient.

5. The system of claim 1 further comprising a temperature sensor, associated with the second pressure sensor, measuring and providing a temperature data from the abdominal region of the patient, wherein the first pressure data from the first sensor is adjusted to remove any temperature related effects by using temperature data from the temperature sensor.

6. The system of claim 1 wherein the delivery member has a communication interface for communication with the external signal processing component of an external data receiving device, a power supply such that the first pressure sensor is provided with power, and the output of the first pressure sensor can be passed through the delivery member communication interface to the external data receiving device, located outside the patient's body.

7. The system of claim 1, wherein the first pressure sensor has a wireless communication transmitter for communication with the external signal processing component via an external data receiving device.

8. The system of claim 1 further comprising an alarm device, contained within the signal processing component, to provide warning if a pressure detected or calculated by the system meets a predetermined condition.

9. The system of claim 1, configured to activate a nerve stimulation device connected to the patient to which the system is itself connected, to stimulate the nervous system of the patient to act in response to a predetermined pressure condition detected or calculated by the system to reduce the body fluid pressure in the bladder.

10. A system for in-vivo monitoring of pressure of a body fluid, the system comprising:
- a delivery component of a cannula type being configured to penetrate through an abdominal wall of the patient and further through a location on the bladder wall into the interior volume;
- a flexible elongate sensor delivery member shaped so as to pass through the delivery component when the delivery component has penetrated the bladder wall in order to allow the sensor delivery member to enter into the interior volume of the bladder; and
- a first pressure sensor being positioned at a distal rounded end region of the delivery member that is inserted into the bladder interior of the patient, the first pressure sensor measuring and providing a first pressure data of the body fluid in the bladder, the first pressure sensor being integrally connected to a distal tip part of a sensor delivery member during insertion through the delivery component into the patient bladder, and the sensor delivery member and the first pressure sensor having lesser diameter than the delivery component;
- a second pressure sensor configured to be inserted subcutaneously into the abdominal region of the patient, the second pressure sensor measuring and providing a second pressure data that may influence the first pressure data; and
- an external signal processing component located remotely from the abdominal wall surface of the patient, configured to receive and process the first pressure data and the second pressure data while the patient is engaged in ambulatory movement, calculate a differential signal between the first pressure data and the second pressure data and automatically adjust the first pressure data based on the calculated differential while the patient is engaged in ambulatory movement, thereby compensating for variations in pressure caused at least in part by the patient's ambulatory movement, and
- the adjustment of the first pressure data based on the calculated differential with the second pressure data being performed based on the readings from the first and second pressure sensors, as received and adjusted while the patient is engaged in the ambulatory movement,
- and the adjustment automatically compensating for the internal organ activity caused by the ambulatory movement of the patient.

11. The system of claim 10, wherein the second pressure data is a reference pressure data and wherein the first pressure data and the reference data are received by the external signal processing component through separate electronic modules.

12. The system of claim 10 further comprising a temperature sensor, associated with the second pressure sensor, measuring and providing a temperature data, wherein the first pressure data, received from the first sensor, is adjusted to remove any temperature related effects by using the temperature data from the temperature sensor.

13. The system of claim 10 wherein the delivery member has a communication interface for communication with the external signal processing component via an external data receiving device, and a power supply such that the first pressure sensor is provided with power and the output of the first pressure sensor can be passed through the delivery member communication interface to the external data receiving device, located outside the patient's body.

14. The system of claim 10, wherein the first pressure sensor has wireless communication transmitter for communication with the external signal processing component via an external data receiving device.

15. The system of claim 10 further comprising an alarm device, contained within the signal processing component, to provide warning if a pressure detected or calculated by the system meets a predetermined condition.

16. The system of claim 10, configured to activate a nerve stimulation device connected to the patient to which the system is itself connected, to stimulate the nervous system of the patient to act in response to a predetermined pressure condition detected by the system to reduce the body fluid pressure in the bladder.

17. A system for in-vivo monitoring of pressure of a body fluid in a urinary bladder of a patient, the system comprising:
- a delivery component of a cannula type configured to be penetrable through an abdominal wall of the patient and further through a wall of the bladder interior;
- a flexible elongate sensor delivery member shaped so as to pass through the delivery component when the delivery component has penetrated the bladder wall in order to allow the sensor delivery member to enter into the bladder of the patient; and
- a first pressure sensor positioned at a distal rounded end of the delivery member that is inserted into the bladder interior, the first pressure sensor measuring and providing a first pressure data of the body fluid inside the bladder;
- a second pressure sensor configured to be inserted subcutaneously into the abdominal region adjacent the bladder or into another organ that is different from the bladder,
- an external signal processing component located remotely from the abdominal wall of the patient, configured to receive and process the first pressure data while the patient is engaged in ambulatory movement,
- wherein the first pressure data and the second pressure data are received by the external processing component through separate electronic modules and to be calculated into a differential signal, and
- wherein the external signal processing component provides an output to a user based upon the received first pressure data and the calculated differential signal.

18. The system of claim 17,
- wherein the external signal processing component is configured to receive and process the first pressure data and the second pressure data while the patient is engaged in ambulatory movement, calculate a differential signal between the first pressure data and the second pressure data and automatically adjust the first pressure data based on the calculated differential while the patient is engaged in ambulatory movement, thereby compensating for variations in pressure caused at least in part by the patient's ambulatory movement, and
- wherein the adjustment of the first pressure data based on the calculated differential with the second pressure data is performed based on the readings from the first and second pressure sensors, and the adjustment automatically compensates for the internal organ activity caused by the ambulatory movement of the patient, received and adjusted while the patient is engaged in ambulatory movement comprising walking, running, daily movements and peristaltic movement of the internal organ.

19. The system of claim 18, further comprising a temperature sensor, associated with the second pressure sensor, measuring and providing a temperature data, wherein the first pressure data from the first sensor is adjusted to remove any temperature related effects by using temperature data from the temperature sensor.

20. The system of claim 17, wherein the sensor delivery member has lesser diameter than the delivery component, and the first pressure sensor is integrally connected to a tip part of the sensor delivery member during insertion through the delivery component into the bladder interior.

21. The system of claim 17, wherein the delivery member has a communication interface for communication with the external signal processing component via an external data receiving device, a power supply such that the first pressure sensor is provided with power, and the output of the first pressure sensor can be passed through the delivery member communication interface to the external data receiving device, located outside the patient's body.

22. The system of claim 17, wherein the first pressure sensor has wireless communication transmitter for communication with the external signal processing component via an external data receiving device.

23. The system of claim 17, further comprising an alarm device, contained within the signal processing component, to provide warning if a pressure detected or calculated by the system meets a predetermined condition.

24. The system of claim 17, configured to activate a nerve stimulation device connected to the patient to which the system is itself connected, to stimulate the nervous system of the patient to act in response to a predetermined pressure condition detected or calculated by the system to trigger delivery of urine from the bladder and thereby reduce the fluid pressure.

* * * * *